US012782305B2

(12) United States Patent
Grille et al.

(10) Patent No.: US 12,782,305 B2
(45) Date of Patent: Nov. 3, 2026

(54) FLUID SENSOR FOR DETECTING A TARGET FLUIDS

(71) Applicant: Infineon Technologies AG, Neubiberg (DE)

(72) Inventors: Thomas Grille, Nötsch im Gailtal (AT); Gerald Stocker, Goritschach (AT); Thomas Krotscheck Ostermann, Oberwinklern (AT); Pooja Thakkar, Villach (AT); David Tumpold, Kirchheim beim München (DE); Reyhaneh Jannesari, Plesching (AT)

(73) Assignee: Infineon Technologies AG, Neubiberg (DE)

( * ) Notice: Subject to any disclaimer, the term of this patent is extended or adjusted under 35 U.S.C. 154(b) by 196 days.

(21) Appl. No.: 18/420,325

(22) Filed: Jan. 23, 2024

(65) Prior Publication Data

US 2024/0255450 A1 Aug. 1, 2024

(30) Foreign Application Priority Data

Jan. 26, 2023 (EP) .................................... 23153376

(51) Int. Cl.
*G01N 25/18* (2006.01)
*G01N 1/44* (2006.01)
*G01N 33/00* (2006.01)

(52) U.S. Cl.
CPC ............... *G01N 25/18* (2013.01); *G01N 1/44* (2013.01); *G01N 33/0027* (2013.01)

(58) Field of Classification Search
CPC ...... G01N 25/18; G01N 1/44; G01N 33/0027; G01N 33/004; G01N 2201/0686;
(Continued)

(56) References Cited

U.S. PATENT DOCUMENTS

2016/0231244 A1* 8/2016 Camargo ............. G01N 21/031
2020/0309686 A1* 10/2020 Grille ................ G01N 21/3504
(Continued)

FOREIGN PATENT DOCUMENTS

EP 3715829 A1 9/2020
WO WO-2007074348 A2 * 7/2007 ........... G01N 21/552
WO 2017003353 A1 1/2017

OTHER PUBLICATIONS

Siebert, R., et al., "Infrared Integrated Optical Evanescent Field Sensor for Gas Analysis", Sensors and Actuators A: Physical, Elsevier BV, NL, vol. 119, No. 1, Mar. 28, 2005, 12 pages.

*Primary Examiner* — John E Breene
*Assistant Examiner* — Manuel Salvador Castellon, Jr.
(74) *Attorney, Agent, or Firm* — Slater Matsil, LLP

(57) ABSTRACT

A fluid sensor detects a target fluid and comprises thermal radiation emitters emitting a broadband thermal radiation, a waveguide structure guiding the thermal radiation comprising an evanescent field component, an optical filter structure coupled to the waveguide structure to provide a filtered thermal radiation having a center wavelength, a thermal radiation detector configured to provide a detector output signal based on a radiation strength of the filtered thermal radiation, and an actuation device for connecting the plurality of thermal radiation emitters with a power source such that the plurality of thermal radiation emitters has an operating temperature between 400 to 1300 K.

20 Claims, 9 Drawing Sheets

A: Exemplaric placement of filter: close to detector

B: Exemplaric placement of filter: close to emitter

(58) Field of Classification Search
CPC ........... G01N 21/3504; G01N 21/3577; G01N 21/552; G01N 21/255; G01N 2021/3129; G01N 2201/0806
See application file for complete search history.

(56) References Cited

U.S. PATENT DOCUMENTS

2022/0276154 A1* 9/2022 Le ...................... G01N 33/0006
2022/0381659 A1 12/2022 Stocker et al.

* cited by examiner

A: Exemplaric placement of filter: close to detector

B: Exemplaric placement of filter: close to emitter

| temperature [K] | peak wavelength [µm] | total in-band power [W] - 1 emitter | total in-band power [W] - 4 emitters | total in-band power [W] - 8 emitters |
|---|---|---|---|---|
| 500 | 5.79 | 7.4 E-9 | 2.9 E-8 | 5.9 E-8 |
| 600 | 4.83 | 2.2 E-8 | 9.1 E-8 | 1.8 E-7 |
| 700 | 4.14 | 5.1 E-8 | 2.0 E-7 | 4.1 E-7 |
| 800 | 3.62 | 9.4 E-8 | 3.7 E-7 | 7.5 E-7 |
| 900 | 3.22 | 1.5 E-7 | 6.1 E-7 | 1.2 E-6 |
| 1000 | 2.90 | 2.2 E-7 | 9.0 E-7 | 1.8 E-6 |
| 1100 | 2.63 | 3.1 E-7 | 1.2 E-6 | 2.5 E-6 |
| 1200 | 2.41 | 4.0 E-7 | 1.6 E-6 | 3.2 E-6 |
| 1300 | 2.23 | 5.1 E-7 | 2.0 E-6 | 4.1 E-6 |

Fig. 2b

FLUID SENSOR FOR DETECTING A TARGET FLUIDS

This application claims the benefit of European Patent Application No. 23153376, filed on Jan. 26, 2023, which application is hereby incorporated herein by reference.

TECHNICAL FIELD

Embodiments relate in general to the field of sensor devices and, more specifically, to the field of fluid sensors for detecting target fluids.

BACKGROUND

The detection of environmental conditions, e.g. gas components, in the ambient atmosphere is becoming increasingly important in the implementation of appropriate sensors within mobile devices, for example, but also in the application in home automation, such as smart homes, and, for example, in the automotive sector. The field of monitoring the air quality and the gas composition in our environment receives more and more attention. However, with the extensive use of sensors, there is also a particular need to be able to produce such sensors cost-effectively, where the resulting reliability and accuracy of the sensors should be as high as possible.

Generally, there is a need in the art for an approach to implement improved fluid sensors having low fabrication requirements and providing an adequate sensitivity for the target fluid to be detected by the sensor device.

SUMMARY

According to an embodiment, a fluid sensor for detecting a target fluid comprises a plurality of thermal radiation emitters for emitting a broadband thermal radiation, a waveguide structure configured to guide the emitted thermal radiation emitted from the plurality of thermal radiation emitters, where the guided thermal radiation comprises an evanescent field component for interacting with the surrounding atmosphere comprising the target fluid, an optical filter structure coupled to the waveguide structure, where the optical filter structure is configured to filter the broadband thermal radiation emitted by the thermal radiation emitter and to provide a filtered thermal radiation having a center wavelength ($\lambda_o$), a thermal radiation detector configured to provide a detector output signal based on a radiation strength of the filtered thermal radiation received from the waveguide structure, and an actuation device for connecting the plurality of thermal radiation emitters with a power source for providing the thermal radiation emitters in an actuated condition with electric energy so that the plurality of thermal radiation emitters has an operating temperature between 400 to 1300 K.

According to an embodiment, the operating temperature of the plurality of thermal radiation emitters may be adjusted so that an absorption band or spectral line of the target fluid is within a (tolerance) range of ±10% at a peak intensity value of the IR emission spectrum of the plurality of thermal radiation emitters.

According to an embodiment, the waveguide structure may comprise a plurality of waveguides, where a respective one of the plurality of thermal radiation emitters is optically coupled to one of the plurality of waveguides, and where the outputs of the plurality of waveguides are coupled to the thermal radiation detector.

According to an embodiment, a multi-fluid sensor comprises the above fluid sensor, where the waveguide structure comprises a plurality of waveguides, where a respective one of the plurality of thermal radiation emitters is optically coupled to a respective one of the plurality of waveguides, and where the optical filter structure comprises a plurality of optical filter elements. A first group of the optical filter elements, which is optically coupled to a first group of the plurality of waveguides, is configured to filter the broadband thermal radiation of the first group of thermal radiation emitters to provide a filtered thermal radiation having a first center wavelength ($\lambda_1$), and a second group of the optical filter elements, which is optically coupled to a second group of the plurality of waveguides, is configured to filter the broadband thermal radiation of the second group of thermal radiation emitters to provide a filtered thermal radiation having a second center wavelength ($\lambda_2$).

According to an embodiment, the first center wavelength ($\lambda_1$) may correspond to an absorption band of a first target fluid, and where the second center wavelength ($\lambda_2$) may correspond to an absorption band of a second target fluid.

BRIEF DESCRIPTION OF THE DRAWINGS

Embodiments of a fluid sensor and a multi-fluid sensor are described herein in detail with respect to the appended drawings and figures, in which:

FIG. 2*b* shows a matrix indicating the in-band power for different emitter configurations as a function of the temperature;

In the following description, embodiments are discussed in further detail using the figures, where in the figures and the specification identical elements and elements having the same functionality and/or the same technical or physical effect are provided with the same reference numbers or are identified with the same name. Thus, the description of these elements and of the functionality thereof as illustrated in the different embodiments are mutually exchangeable or may be applied to one another in the different embodiments.

DETAILED DESCRIPTION

In the following description, embodiments are discussed in detail, however, it should be appreciated that the embodiments provide many applicable concepts that can be embodied in a wide variety of semiconductor devices. The specific embodiments discussed are merely illustrative of specific embodiments for descriptive purposes that do not limit the scope of the disclosed embodiments. In the following description of embodiments, the same or similar elements having the same function have associated therewith the same reference signs or the same name, and a description of such elements may not be repeated for every embodiment. Moreover, features of the different embodiments described hereinafter may be combined with each other.

In the description of the embodiments, terms and text passages placed in brackets (next to a described element or function) are to be understood as further explanations, exemplary configurations, exemplary additions and/or exemplary alternatives of the described element or function.

It is understood that when an element is referred to as being "connected" or "coupled" to another element, it may be directly connected or coupled to the other element, or intermediate elements that may be present. Conversely, when an element is referred to as being "directly" connected to another element, "connected" or "coupled," there are no intermediate elements. Other terms used to describe the relationship between elements should be construed in a similar fashion (e.g., "between" versus "directly between", "adjacent" versus "directly adjacent", and "on" versus "directly on", etc.).

For facilitating the description of the different embodiments, some of the figures comprise a Cartesian coordinate system x, y, z, where the x-y-plane corresponds, i.e. is parallel, to a main surface region (=a reference plane=x-y-plane) of a substrate, for example, where the direction vertically up with respect to the reference plane (x-y-plane) corresponds to the "+z" direction, and where the direction vertically down with respect to the reference plane (x-y-plane) corresponds to the "−z" direction. In the following description, the term "lateral" means a direction parallel to the x- and/or y-direction or a direction parallel to (or in) the x-y-plane, where the term "vertical" means a direction parallel to the z-direction.

Figure 1A:
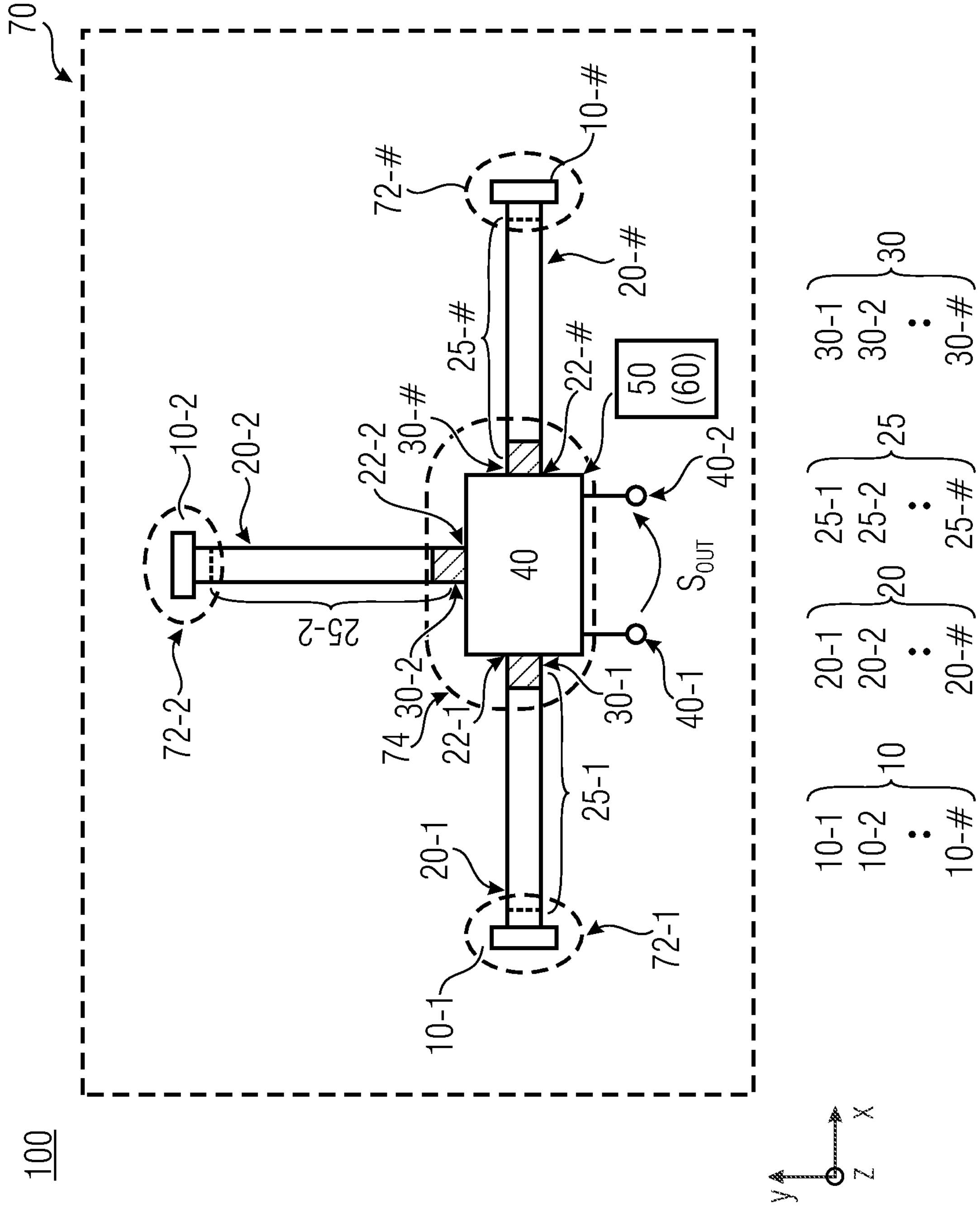
FIGS. 1*a*-1*c* show a schematic top view of a fluid sensor according to an embodiment.
Figure 1B:
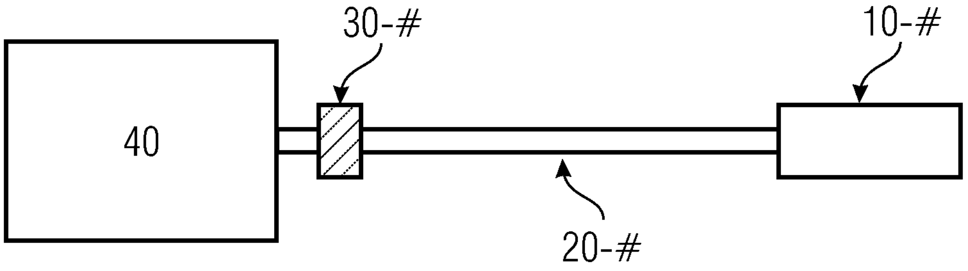
Figure 1B:
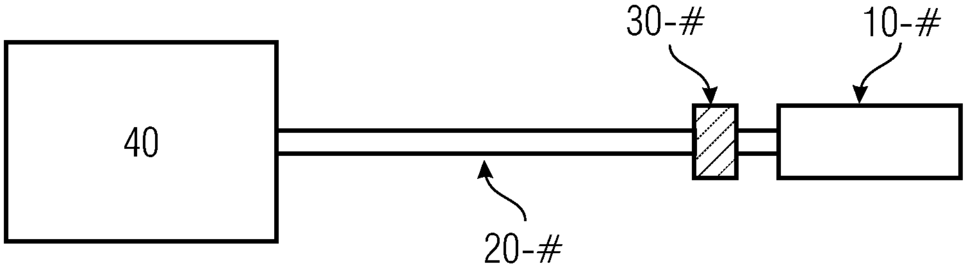
Figure 1C:
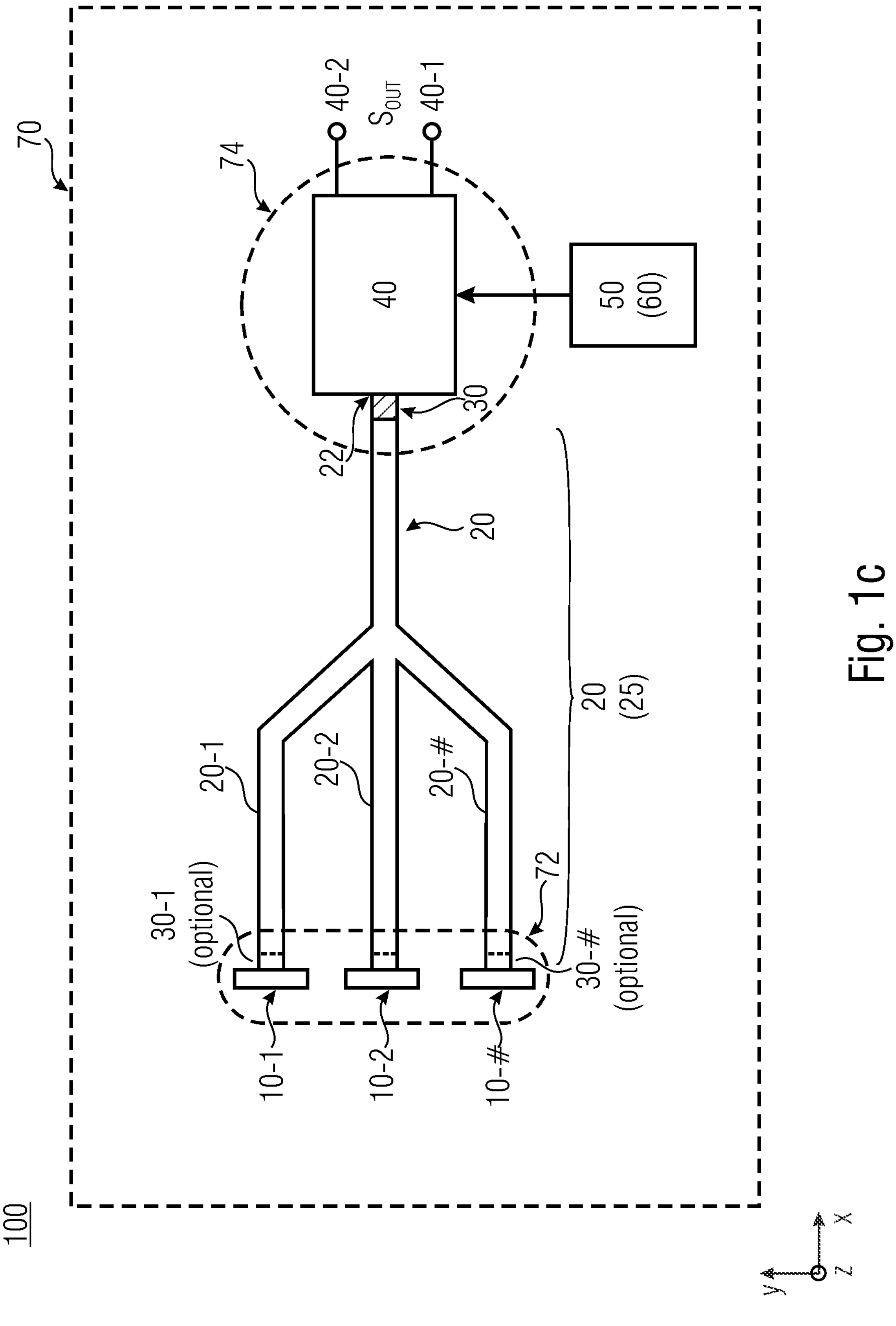

FIGS. 1*a*-1*c* show a schematic top view of a fluid sensor 100 for detecting a target fluid Fr according to an embodiment.

The fluid sensor 100 is arranged for sensing an amount or a concentration of a target fluid or a target fluid component Fr in the surrounding atmosphere, e.g. an environmental medium. In the present context, the term "fluid" may relate to a liquid or a gas. In case the environmental medium relates to environmental air, the target fluid may relate to a target gas or a target gas component which is present in the environmental air. The present disclosure is applicable to sensing a target liquid or a target liquid component in the environmental medium (fluid).

As shown in FIGS. 1*a*-1*c*, the fluid sensor 100 comprises a plurality of (at least two) thermal radiation emitters 10-1, 10-2, . . . , 10-# (# is a placeholder for an integer greater-than-or-equal to two; #≥2) for emitting a broadband thermal radiation R. The fluid sensor 100 further comprises a waveguide structure 20 (=20-1, 20-2, . . . , 20-# in FIG. 1*a* or 20', 20-1, 20-2, . . . , 20-# in FIG. 1*c*) configured to guide the emitted thermal radiation R which is emitted from the plurality of thermal radiation emitters 10-1, 10-2, . . . , 10-# where the guided thermal radiation R comprises an evanescent field component for interacting with the surrounding atmosphere (medium) comprising the target fluid $F_T$.

The fluid sensor 100 further comprises an optical filter structure 30 (=30-1, 30-2, . . . , 30-#) which is coupled to the waveguide structure 20. The optical filter structure 30 is configured to filter the broadband thermal radiation R which is emitted by the thermal radiation emitters 10, and to provide a filtered thermal radiation $R_F$ having a center wavelength $\lambda_o$.

As exemplarily shown in FIG. 1*b*, the optical filter structure 30 (=30-1, 30-2, . . . , 30-#) may be placed close to the detector 40 (example A of FIG. 1*b*) or the optical filter structure 30 (=30-1, 30-2, . . . , 30-#) may be placed close to the thermal radiation emitters 10-# (example B of FIG. 1*b*). In case, the optical filter structure 30 with the filter elements 30-1, 30-2, . . . , 30-# is placed close to the thermal radiation emitter 10-#, the emitted light (thermal radiation R) would be directly (after emission) filtered already, where the remaining 1% inband light would be transmitted towards the detector 40. So, the light (thermal radiation R) becomes selective immediately. The arrangement of example B may save about a light energy of 99% unwanted and unfiltered light compared to the arrangement of example A.

The fluid sensor 100 further comprises a radiation detector 40 which is configured to provide a detector output signal Sour based on a radiation strength of the filtered thermal radiation $R_F$ which is received by the thermal radiation detector 40 from the waveguide structure 20. The fluid sensor 100 further comprises an actuation device 50 for connecting the plurality of thermal radiation emitters 10 with a power source 60 for providing the thermal radiation emitters 10 in an actuated condition with electric energy so that the plurality of thermal radiation emitters 10 has an operating temperature between 400 and 1300 K.

As shown in FIG. 1*a*, the waveguide structure 20 may comprise a plurality of waveguides 20-1, 10-2, . . . , 10-#, where a respective one of the plurality of thermal radiation emitters 10-1, 10-2, . . . , 10-# is optically coupled to one of the plurality of waveguides 20-1, 20-2, . . . , 20-#, and where the outputs 22-1, 22-2, . . . , 22-# of the plurality of waveguides 20-1, 20-2, . . . , 20-# are coupled to the thermal radiation detector 40.

According to embodiments, the waveguides 20-1, 20-2, . . . , 20-# of the waveguide structure 20 extend or pass through the interaction area (region) 25 (=25-1, . . . , 25-#), where the waveguides 20-1, 20-2, . . . , 20-# of the waveguide structure 20 are surrounded by or in contact with the surrounding atmosphere. Thus, the waveguides 20-1, 20-2, . . . , 20-# of the waveguide structure 20 guide the thermal radiation R having the evanescent field component through the interaction area 25, where the evanescent field components of the guided radiation interact with the surrounding atmosphere comprising the target fluid $F_T$.

Each of the waveguides (or waveguide branches) 20-1, 20-2, . . . , 20-# of the waveguide structure 20 may comprise the optical filter structure 30-1, 30-2, . . . , 30-# to filter the broadband thermal radiation R emitted by each of the thermal radiation emitters 10-1, 10-2, . . . , 10-# and to provide a filtered thermal radiation RF having the center wavelength $\lambda_o$.

As exemplarily shown in FIG. 1*c*, the waveguide structure 20 may comprise according to a further embodiment a joint waveguide (common waveguide) 20', where the broadband thermal radiation R of the plurality of thermal radiation emitters 10-1, 10-2, . . . , 10-# is coupled into the joint waveguide 20', and where the output 22 of the joint waveguide 20' is coupled to the thermal radiation and detector 40. Thus, a plurality of branches (separate segments or sections) 20-1, 20-2, . . . , 20-# of the waveguide structure 20 may be merged to form the joint waveguide 20'.

According to an embodiment, the waveguide structure 20 having the joint waveguide (common waveguide) may extend or pass through the interaction area 25, where the waveguide structure 20 is surrounded by or in contact with the surrounding atmosphere. Thus, (1.) the branches 20-1, 20-2, . . . , 20-# of the waveguide structure 20, (2.) the branches 20-1, 20-2, . . . , 20-# of the waveguide structure 20 and the joint waveguide 20', (3.) by the joint waveguide 20' may extend or pass through the interaction area (region) 25, where the evanescent field component of the waveguide structure 20 interacts with the surrounding atmosphere comprising the target fluid Fr. Moreover, the optical filter structure 30 may be arranged in each of the branches 20-1, 20-2, . . . , 20-# of the waveguide structure 20 or in the joint waveguide structure 20.

Having a plurality of (optically parallel) waveguides (waveguide branches) 20-1, 20-2, . . . , 20-#, which extend or pass through the interaction area 25, may provide a high (e.g. an increased) efficiency of sensing in the evanescent field as the effective interaction area (interaction length) with the surrounding atmosphere is high (e.g. increased, when compared to a joint waveguide structure).

According to the embodiment of FIGS. 1*a*-1*c*, the waveguide structure 20 may comprise, for example, a semiconductor material or a dielectric material, and is configured to guide the IR radiation R by total reflection. The guided IR radiation R comprises an evanescent field component, i.e., a field component outside the waveguide structure 20, for interacting with the surrounding atmosphere comprising the target fluid $F_T$, i.e., a target liquid or a target gas. The interaction of the evanescent field component with the surrounding atmosphere can result in a reduction of the transmitted thermal radiation R (in the absorption band or spectral line of the target fluid FT) due to absorption of the guided radiation R (in the absorption band or spectral line of the target fluid FT). The (degree of) absorption can be a measure for the target fluid concentration in the surrounding atmosphere or medium.

According to an embodiment, the operating temperature T of the plurality of thermal radiation emitters 10 (=10-1, 10-2, . . . , 10-#) is adjusted (e.g. by the actuation device 50), so that an absorption band or spectral line of the target fluid Fr is within a range (tolerance range) of +/−10%, +/−5% or +/−2% at a peak intensity value of the IR emission spectrum of the plurality of thermal radiation emitters 10-1, 10-2, . . . , 10-#.

The range (tolerance range) of +/−10%, +/−5% or +/−2% may relate to the wavelength $\lambda_{BAND}$ of the absorption band or spectral line of the target fluid $F_T$ with respect to the wavelength $\lambda_{PEAK}$ of the peak intensity value of the emission spectrum, for example with $1.1 \geq \lambda_{BAND}/\lambda_{PEAK} \geq 0.9$; $1.05 \geq \lambda_{BAND}/\lambda_{PEAK} \geq 0.95$; or $1.02 \geq \lambda_{BAND}/\lambda_{PEAK} \geq 0.98$. Alternatively, the range (tolerance range) of +/−10%, +/−5% or +/−2% may relate to the peak intensity value $I_{MAX}$ of the emission spectrum, where the wavelength $\lambda_{BAND}$ of the absorption band or spectral line of the target fluid $F_T$ range is at a position where the emission spectrum has at least 90%, 95% or 98% of its peak intensity value $I_{MAX}$ of the thermal radiation R.

Figure 2A:
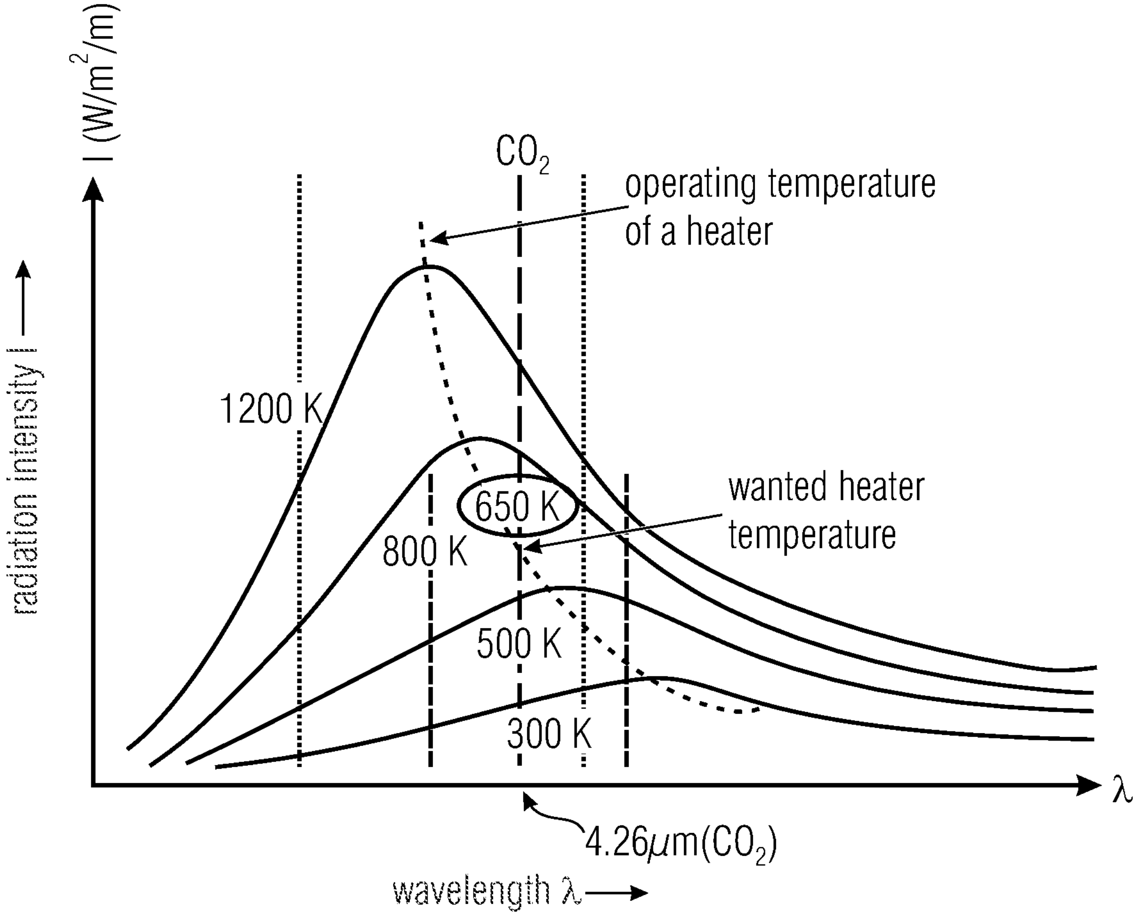
FIG. 2*a* shows an emission spectrum for a black body emitter at different temperatures according to Planck's Law and Wien's Displacement Law.

With respect to the chosen peak intensity value of the IR emission spectrum of the plurality of thermal radiation emitters 10 (10-1, 10-2, . . . , 10-#) FIGS. 2*a*-2*b* are referred to.

FIG. 2*a* shows an emission spectrum (e.g., spectral power density or radiation intensity) for a black body emitter 10-1, . . . , 10-# at different temperatures T according to Planck's Law and Wien's Displacement Law. Wien's displacement law states that the black-body radiation curve for different temperatures peaks at different wavelengths that are inversely proportional to the temperature T. The shift of that peak is a direct consequence of Planck radiation law, which describes the spectral brightness or intensity of black-body radiation as a function of wavelength at any given temperature.

In the following exemplary embodiment, the detection of carbon dioxide ($CO_2$) as the target fluid $F_T$ is described, where carbon dioxide ($CO_2$) has its absorption band or spectral line approximately at 4.26 μm or in a range between 4.14 and 4.35 μm.

Using a temperature range of about 1200 K for operating the thermal emitters 10 would provide a sufficient radiation intensity "I" of the emitted broadband thermal radiation R. However, according to Plank's law or Wien's distribution law, at 1200 K, the proportion of the $CO_2$ wavelength (absorption band or spectral line) of 4.26 μm is a small proportion of the overall emitted radiation. Other wavelengths (and the wavelength range around the peak intensity value) outside a narrow spectral range around 4.26 μm can react with other gases than $CO_2$. Thus, unwanted cross-sensitivities can occur.

Thus, the fluid sensor 100 can include a plurality (e.g. at least 2 or 3, 4, 5, 6, 7, 8 or more) of thermal radiation emitters 10-1, . . . , 10-#, where the operating temperature T of the plurality of thermal radiation emitters 10-1, 10-2, . . . , 10-# is adjusted, so that an absorption band or spectral line of the target fluid Fr is within a range of +/−10% or less (e.g. +/−5% or +/−2%) at a peak intensity value of the IR emission spectrum of the plurality of thermal radiation emitters 10.

Thus, using a plurality of thermal radiation emitters 10 having an operating temperature T, so that the peak intensity value of the IR emission spectrum corresponds to the absorption band or spectral line of the target fluid $F_T$, provides a sufficient radiation intensity "I" of the emitted broadband thermal radiation R. According to Plank's law or Wien's distribution law, at 700K, the proportion of the $CO_2$ wavelength 4.26 μm is a large proportion of the overall emitted radiation. Other wavelengths outside a narrow spectral range around 4.26 μm can react with other gases than $CO_2$ in a reduced way. Thus, unwanted cross-sensitivities can be avoided or at least effectively reduced.

According to embodiments, the fluid sensor 100 may be implemented as a mid-wave infrared radiation sensors (MIRS). The MIRS 100 comprises the plurality of thermal radiation emitters (sources) 10, which emit, in the black body spectrum, the broadband IR radiation R. The radiation R is coupled into the waveguides 20-1, . . . , 20-#. For achieving the filtered (monochromatic) IR radiation RF, the respective filter structures 30-1, . . . , 30-#, e.g. photonic crystal filters, are respectively coupled to or implemented in the waveguides 20-1, . . . , 20-# for transmitting the required wavelength. In case, carbon dioxide $CO_2$ is the target gas, the filter structures may be optimized for the wavelength (e.g., the absorption band or spectral line) of 4.26 μm (+/−2%). The IR radiation R is coupled in the waveguide and a surrounding evanescent field is formed, where the wavelength of the radiation R in the absorption band or spectral line of the target gas $F_T$ is absorbed, e.g. by the $CO_2$ in the ambient atmosphere. The reduction of the intensity of the radiation R in the wavelength (range) of the absorption band or spectral line of the target gas is a measure for the concentration of target gas $F_T$, such as $CO_2$.

Due to the utilization of the plurality of thermal emitters 10-1, . . . , 10-#, a relatively low temperature (e.g. 650 K or 700 K) is used at the thermal emitters 10-1, . . . , 10-# in order to pass through the waveguide structure 20 with a sufficient amount of heat. Moreover, according to Plank's law or Wien's distribution law, at 650 K or 700 K, the proportion of the $CO_2$ wavelength 4.26 μm is a large proportion of the overall emitted radiation R.

Thus, the fluid sensor 100 can ensure a clean (effective) measurement. Thus, a sufficient radiation energy (guided in the waveguides 20) impinges onto the thermal radiation detector 40, e.g. a piezo detector or a pn diode detector, as the attenuation for the wavelength $\lambda_o$ (of the absorption band or spectral line of the target gas) on the path through the waveguides 20 is sufficiently low.

According to the present disclosure, a plurality of thermal heaters 10-1, . . . , 10-# are used as a thermal source in order to bring the necessary amount of heat to the detector 40.

FIG. 2*b* shows a matrix indicating the in-band power for different emitter configurations as a function of the temperature (and the resulting peak temperature). From the matrix of FIG. 2*b* can be derived that a number of four (4) heaters at 800 K and a number of eight (8) heaters at 700 K can roughly equal the emission intensity of a single heater at 1200 K. Four (4) heaters at 1000 K would approximately double the emission intensity of a single heater at 1200 K.

Figure 2C:
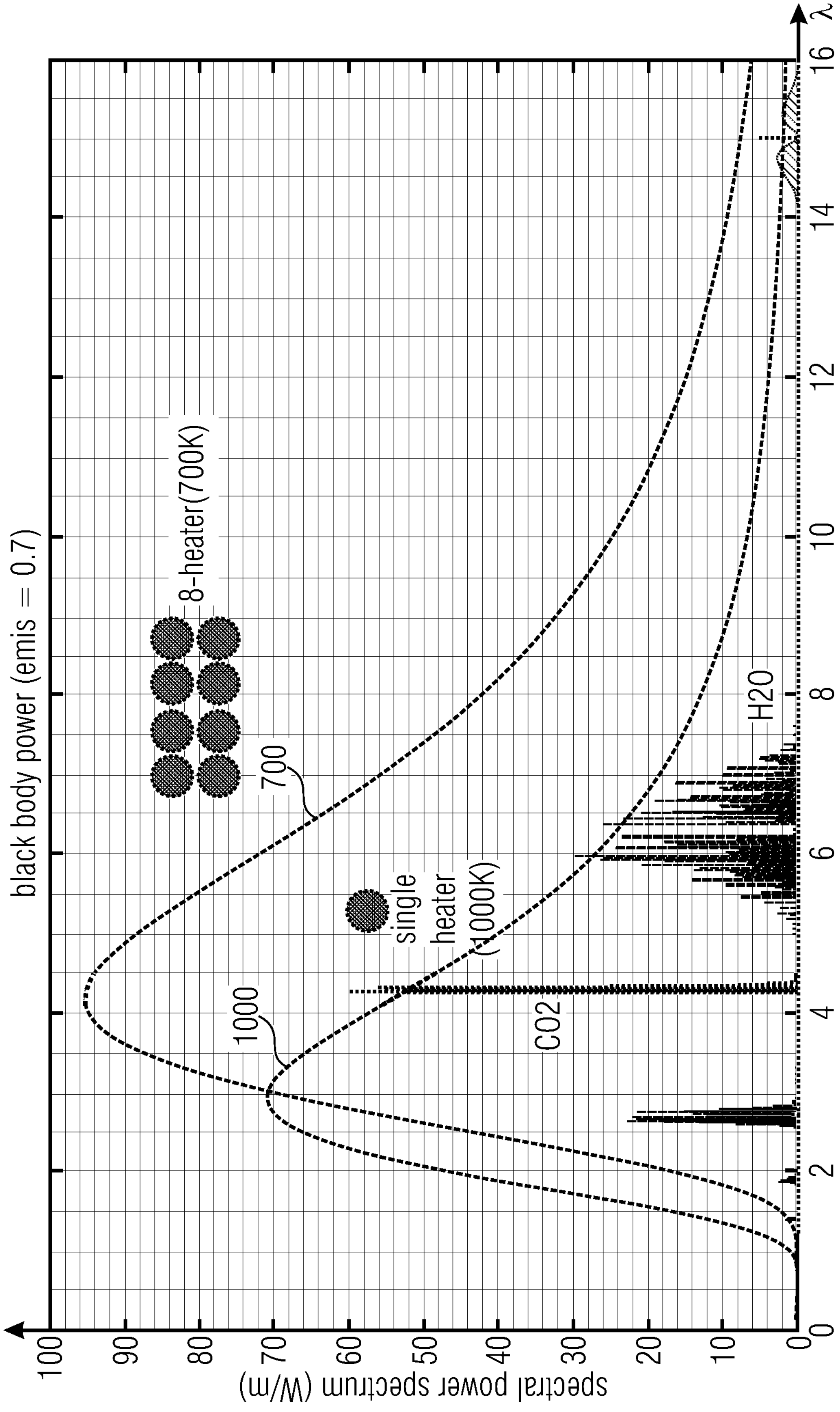
FIG. 2*c* shows an emission spectrum for a single black body emitter at 1000 K and for an emitter arrangement having eight (8) black body emitters at a temperature of 700 K.

FIG. 2*c* shows a (simulated) emission spectrum for a single black body emitter at 1000 K and for an emitter arrangement having eight (8) black body emitters at a temperature of 700 K. The eight (8) black body emitters may comprise the same emission surface area each. According to embodiments, it is derivable from calculations and simulations that approximately 8 (7 or 8) sources (heaters) 10-# can be operated at 700 K to get approximately the same amount of heat at the detector 40 as a comparable emitter at 1200 K. Thus, the combined radiation intensity of 8 (7 or 8) thermal heaters (each) at 700 K approximately corresponds to the radiation intensity of a single thermal heater at 1200 K. The advantage is that the radiation of the cooler emitters, from a spectral point of view, is already clearly better in the intended spectral range around 4.26 μm (due to the less out-of-band radiation). Additionally, the effective waveguide area is enlarged, which results in an increased interaction area 25 for light-gas interaction, which finally makes the sensor more sensible due to an increased signal-to-noise ratio (SNR).

According to an embodiment, the operating temperature T of the plurality of thermal radiation emitters 10-1, 10-2, . . . , 10-# may be adjusted to a temperature range between 550 and 800 K, 600 and 700 K or 620 and 680 K so that the absorption band or spectral line of the target gas, e.g. CO2, O3, . . . (λCO2=4.2, . . . )) is within the range of +/−10%, 5% or 2% at the peak intensity value of the IR emission spectrum of the plurality of thermal radiation emitters 10-1, 10-2, . . . , 10-#.

The following table provides some further examples of target gases and the associated emitter temperatures (for matching the absorption band of the respective target gas).

TABLE 1

| Target Gas | Target - Wavelength | Peak - Temperature |
|---|---|---|
| CO2 | 4.2 um | 689.95 K |
| CO | 4.6 um | 629.95 K |
| CH4 | 2.3 um | 986.75 K |
| H2S | 2.5 um | 885.96 K |
| H2S | 7.0 um | 413.97 K |
| C2H3 | 6.9 um | 591.38 K |

According to further embodiments, the operating temperature T of the plurality of thermal radiation emitters 10-1, 10-2, . . . , 10-# may be adjusted to a temperature range between 400 and 1000 K, so that the absorption band or spectral line of the target gas, e.g. $CO_2$, CO, $CH_4$, H2S, C2H3, . . . (λCO2=4.2, $\lambda_{CO}$=4.6, λCH4=2.3, λH2S=2.5 and 7.0, λC2H3=6.9 . . . ) is within the range of +/−10%, 5% or 2% at the peak intensity value of the IR emission spectrum of the plurality of thermal radiation emitters 10-1, 10-2, . . . , 10-#.

The above evaluations and embodiments are applicable to other target fluids having a different absorption band or spectral line.

According to a further embodiment, the waveguide structure 20 comprises a plurality of waveguides 20-1, . . . , 20-#, where a respective one of the plurality of thermal radiation emitters 10-1, . . . , 10-# is optically coupled to one of the plurality of waveguides 20-1, . . . , 20-#, and where the outputs 22-1, . . . , 22-# of the plurality of waveguides 20-1, . . . , 20-# are coupled to the thermal radiation detector 40. The plurality of waveguides 20-1, . . . , 20-# may be arranged in a star-shaped, radial or radiant configuration, where the outputs 22-1, . . . , 22-# of the plurality of waveguides 20-1, . . . , 20-# are directed to a center region of the fluid sensor 100.

According to an embodiment, the usage of several thermal emitters 10-1, . . . , 10-# allows to implement a round and simultaneously star-shaped structure of the waveguides 20-1, . . . , 20-# of the sensor arrangement 100 having a central detector 40. The diameter (e.g., lateral extension) of the sensor arrangement (fluid sensor) 100 may be in a range between 2 and 10 μm or between 4 and 8 μm.

According to an embodiment, the detector 40 may have the shape of a polygon, such as a hexagon or an octagon. Thereby, the waveguides 20-1, . . . , 20-# can run directly to a polygonal edge at a straight (orthogonal) angle. As a unitary waveguide height of 650-750 nm thickness polysilicon with different wavelengths, a total reflection of the radiation R in the waveguides may be maintained. Therefore, it is possible to measure different target gases $F_T$ e.g., CO2 and O3 with the same system, for example.

According to a further embodiment, the thermal radiation detector 40 may arranged at a center region of the fluid sensor 100. According to an embodiment, the thermal radiation detector 40 may be formed as a polygon, so that a respective one of the plurality of waveguides 20-1, . . . , 20-# reaches one of the polygon edges of the detector 40 in an orthogonal angle.

According to a further embodiment, the thermal radiation detector 40 may comprise a pyroelectric temperature sensor, a piezoelectric temperature sensor, a pn junction temperature sensor or a resistive temperature sensor.

According to a further embodiment, the optical filter structure 30 may comprise a plurality of optical filter elements 30-1, . . . , 30-#, where each of the plurality of waveguides 20-1, . . . , 20-# comprises (at least) one of the optical filter elements 30-1, . . . , 30-# to filter the broadband thermal radiation R and to provide the filtered thermal radiation $R_F$ having the center wavelength $\lambda_o$.

According to a further embodiment, the filter elements 30-1, . . . , 30-# of optical filter structure 30 may be formed as optical resonator elements having a narrow transmission band with a center wavelength $\lambda_o$, and where the optical filter structure 30 comprises a photonic crystal structure or a Bragg filter structure as wavelength selective optical elements for providing the filtered thermal radiation $R_F$ having the center wavelength $\lambda_o$.

According to embodiments, the optical filter elements 30-1, . . . , 30-# of the optical filter structure 30 may be formed at any position or intermediate position between the thermal emitters 10-1, . . . , 10-# and the thermal detector.

In FIG. 1*a*-1*b*, it is exemplarily shown, that the optical filter elements 30-1, . . . , 30-# of the optical filter structure 30 are formed between the waveguides 20-1, . . . , 20-# and the thermal detector 40 (e.g. close to the to the detector 40). As exemplarily shown in FIG. 1*b* (example A), the optical filter structure 30 (e.g., 30-1, 30-2, . . . , 30-#) may be placed close to the detector 40. According to a further embodiment, the optical filter elements 30-1, . . . , 30-# of the optical filter structure 30 may be also formed between the thermal emitters 10-1, . . . , 10-# and the waveguides 20-1, . . . , 20-# (e.g. close to the thermal radiation emitters 10-#). As exemplarily shown in FIG. 1*b* (example B), the optical filter structure 30 (e.g., 30-1, 30-2, . . . , 30-#) may be placed close to the thermal radiation emitters 10-#.

In FIG. 1*c*, it is exemplarily shown, that the optical filter structure 30 is formed between the waveguides 20-1, . . . , 20-# and the thermal detector 40 (e.g. close to the detector 40). As exemplarily shown in FIG. 1*c*, the optical filter structure 30 (e.g., 30-1, 30-2, . . . , 30-#) may be placed close to the detector 40. According to a further embodiment, the optical filter elements 30-1, . . . , 30-# of the optical filter structure 30 may be also formed between the thermal emitters 10-1, . . . , 10-# and the waveguides 20-1, . . . , 20-# (e.g. close to the thermal radiation emitters 10-#). As optionally shown in FIG. 1*c*, the optical filter elements 30-1, 30-2, . . . , 30-# may be optionally placed close to the thermal radiation emitters 10-#.

According to a further embodiment, the thermal radiation emitters 10-1, . . . , 10-# may comprise a semiconductor strip having a main emission surface region emitting a broadband thermal radiation in a main radiation emission direction and parallel or vertical to the waveguide structure.

According to a further embodiment, the coupling direction between the waveguide structure 20 and the thermal detector 40 may be parallel (in-plane) or vertical to the propagation direction of to the waveguide structure.

According to a further embodiment, the plurality of waveguides 20-1, . . . , 20-# of the waveguide structure 20 may comprise strip waveguides, slot waveguides or rip waveguides.

According to an embodiment, the fluid sensor 100 may be arranged on a substrate 70 which may form a common system plane for the sensor. The different elements of the fluid sensor 100 may be arranged on the substrate.

The thermal radiation emitters 10 may comprise a semiconductor strip for emitting a broadband thermal radiation R, e.g., a broadband IR radiation. At least a part of the emitted thermal radiation R is coupled into the respective waveguide 20-1, . . . , 20-# of the waveguide structure 20, where the emitted thermal radiation is infrared (IR) radiation or comprises infrared (IR) radiation. The thermal radiation emitters may comprise a semiconductor strip (or a semiconductor wire), where a metallic cover layer may at least partially or completely cover the main emission surface of the semiconductor strip. An optional isolation layer between the metallic layer and the semiconductor wire may be used in order to provide a further homogeneous heating of the device.

According to an embodiment, the substrate 70 may comprises a cavities 72-1, . . . , 72-# vertically below the thermal radiation emitters 10-1, . . . , 10-# 120 and (optionally) below the optical filter elements 30-1, . . . , 30-# structure. According to embodiments, the substrate 70 may also comprise a further cavity 74 vertically below the thermal radiation detector 40. The formation of the cavities in the substrate 70 below the thermal radiation emitters and optionally below the thermal radiation detector reduces the heat transfer from the thermal radiation emitter and/or the thermal radiation detector into the adjacent material so that the emission efficiency of the thermal radiation emitters as well as the detection efficiency of the thermal radiation detector can be increased.

The filter elements (wavelength selective structures) 30-1, . . . , 30-# may be formed as an IR filter, e.g. as a Fabry-Perot filter element (Bragg filter structure), or as a plasmonic structure (photonic crystal structure), e.g. as a plasmonic resonator for the emitted IR radiation.

According to an embodiment, the thermal radiation detector 40 may comprise a pyroelectric temperature sensor, a piezoelectric temperature sensor, a pn junction temperature sensor or a resistive temperature sensor. In case of a pyroelectric temperature sensor (e.g., passive infrared sensor PIR), the thermal detector 40 may comprises a temperature sensitive layer of a piezoelectric semiconductor crystal on a radiation absorbing layer, where a temperature change in the radiation absorbing layer and, thus, in the piezoelectric semiconductor crystal leads to a measurable change in the electrical voltage $S_{OUT}$ (e.g., generated electric charge) between the output terminal 40-1, 40-2. The output signal $S_{OUT}$ may be converted by a high impedance amplifier, for example, into an amplified electrical output signal.

Figure 3:
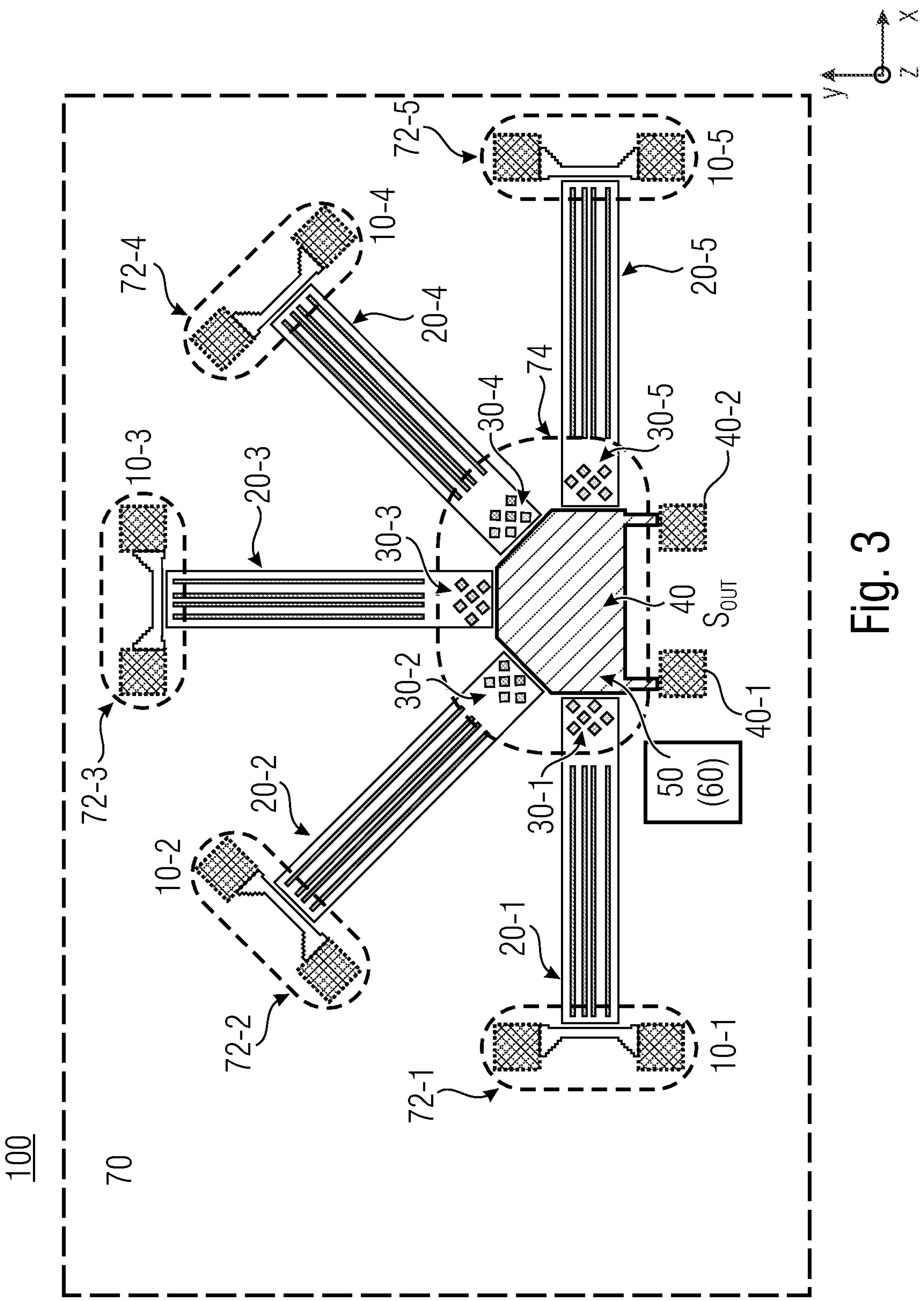
FIG. 3 shows a schematic top view of an implementation of a fluid sensor according to an embodiment.

FIG. 3 shows a schematic top view of an implementation of a fluid sensor 100 according to a further embodiment. The above evaluations of FIGS. 1 and 2*a*-2*c* of the elements of the fluid sensor device 100 and of the functionality thereof are applicable to the corresponding elements of the fluid sensor 100 of FIG. 3.

As shown in FIG. 3, the fluid sensor 100 comprises a plurality of thermal radiation emitters 10 (e.g., 10-1, 10-2, . . . , 10-#) for emitting a broadband thermal radiation R. The fluid sensor 100 further comprises a waveguide structure 20 having a plurality of waveguides 20-1, 10-2, . . . , 10-#, an optical filter structure 30 with a plurality of filter elements 30-1, 30-2, . . . , 30-#, and a radiation detector 40 which is configured to provide a detector output signal Sour based on a radiation strength of the filtered thermal radiation $R_F$ which is received by the thermal radiation detector 40 from the waveguide structure 20. The fluid sensor 100 further comprises an actuation device 50 for connecting the plurality of thermal radiation emitters 10 with a power source 60 for providing the thermal radiation emitters 10 in an actuated condition with electric energy so that the plurality of thermal radiation emitters 10 has an operating temperature between 400 and 1300 K.

As shown in FIG. 3, the thermal radiation detector 40 may arranged at a center region of the fluid sensor 100. According to an embodiment, the thermal radiation detector 40 may be formed as a polygon, so that a respective one of the plurality of waveguides 20-1, . . . , 20-# reaches one of the polygon edges of the detector 40 in an orthogonal angle.

As shown in FIG. 3, the plurality (e.g. 3, 4, 5, 7 or 8 or more) of waveguides 20-1, . . . , 20-# may be arranged within a semi-circle or within in a segment of a circle in a star-shaped, radial or radiant configuration, where the outputs 22-1, . . . , 22-# of the plurality of waveguides 20-1, . . . , 20-# are directed to the central detector 40.

As shown in FIG. 3, the semi-circle arrangement (of the waveguides) of the fluid sensor 100 has, for example, five (5) emitters 10-1, . . . , 10-5, five waveguides 20-1, . . . , 20-5, and five filter elements 30-1, . . . , 30-5.

Thus, according to an embodiment, the radial design of the structure (of the fluid sensor 100) comprises on the outside are the heaters 10-1, . . . , 10-# emitting the black body radiation R and couple into the waveguide 20-1, . . . , 20-#. The filter elements (e.g. photonic crystal filters) 30-1, . . . , 30-# are at the end (or at the beginning or at an intermediate position therebetween) of the waveguides 20-1, . . . , 20-#. If different filter elements (e.g. photonic crystal filters) 30-1, . . . , 30-# are used after the heaters 10-1, . . . , 10-#, multi gas measurements are possible, for example carbon dioxide $CO_2$ and ozone $O_3$ as the different target gases (fluids) $F_T$.

Figure 4:
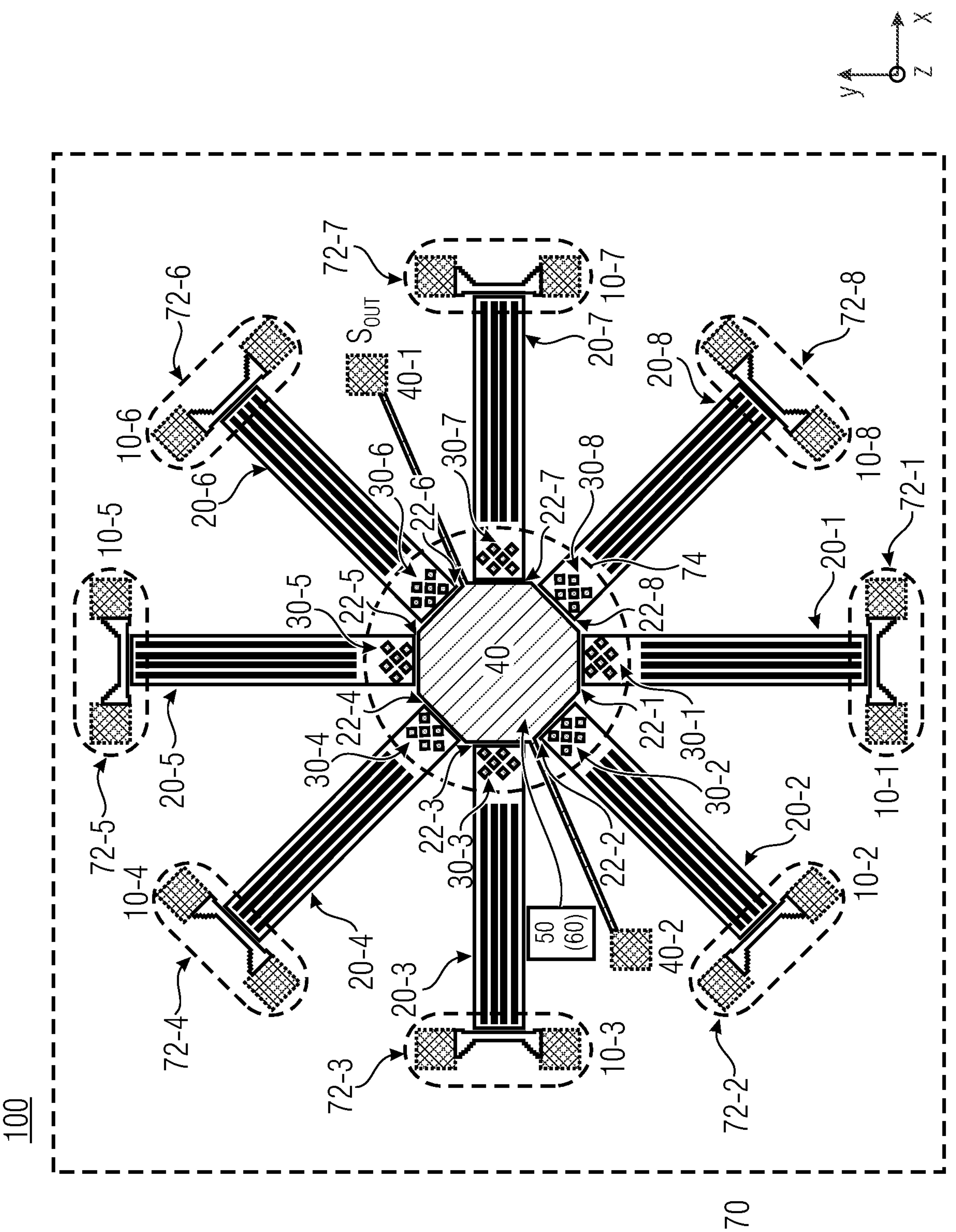
FIG. 4 shows a schematic top view of an implementation of a fluid sensor according to an embodiment.

FIG. 4 shows a schematic top view of a further implementation of a fluid sensor 100 according to a further embodiment. The above evaluations of FIGS. 1, 2a-2c and 3 of the elements of the fluid sensor device 100 and of the functionality thereof are applicable to the corresponding elements of the fluid sensor 100 of FIG. 3.

As shown in FIG. 4, the fluid sensor 100 comprises a plurality of thermal radiation emitters 10 (e.g., 10-1, 10-2, . . . , 10-#) for emitting a broadband thermal radiation R. The fluid sensor 100 further comprises a waveguide structure 20 having a plurality of waveguides 20-1, 10-2, . . . , 10-#, an optical filter structure 30 with a plurality of filter elements 30-1, 30-2, . . . , 30-#, and a radiation detector 40 which is configured to provide a detector output signal Sour based on a radiation strength of the filtered thermal radiation $R_F$ which is received by the thermal radiation detector 40 from the waveguide structure 20. The fluid sensor 100 further comprises an actuation device 50 for connecting the plurality of thermal radiation emitters 10 with a power source 60 for providing the thermal radiation emitters 10 in an actuated condition with electric energy so that the plurality of thermal radiation emitters 10 has an operating temperature between 400 and 1300 K.

As shown in FIG. 4, the thermal radiation detector 40 may arranged at a center region of the fluid sensor 100. According to an embodiment, the thermal radiation detector 40 may be formed as a polygon, so that a respective one of the plurality of waveguides 20-1, . . . , 20-# reaches one of the polygon edges of the detector 40 in an orthogonal angle.

As shown in FIG. 4, the plurality (e.g. 3, 4, 5, 7 or 8) of waveguides 20-1, . . . , 20-# may be arranged within a full circle in a star-shaped, radial or radiant configuration, where the outputs 22-1, . . . , 22-# of the plurality of waveguides 20-1, . . . , 20-# are directed to the central detector 40.

As shown in FIG. 4, the circular arrangement (of the waveguides) of the fluid sensor 100 has, for example, eight (8) emitters 10-1, . . . , 10-8, eight waveguides 20-1, . . . , 20-8, and eight filter elements 30-1, . . . , 30-8.

Thus, according to an embodiment, the radial design of the structure (of the fluid sensor 100) comprises on the outside are the heaters 10-1, . . . , 10-# emitting the black body radiation R and couple into the waveguide 20-1, . . . , 20-#. The filter elements (e.g. photonic crystal filters) 30-1, . . . , 30-# are at the end (or at the beginning or at an intermediate position therebetween) of the waveguides 20-1, . . . , 20-#. If different filter elements (e.g. photonic crystal filters) 30-1, . . . , 30-# are used after the heaters 10-1, . . . , 10-#, multi gas measurements are possible, for example carbon dioxide $CO_2$ and ozone $O_3$ as the different target gases (fluids) $F_T$.

Figures 5A, 5B, 5C:
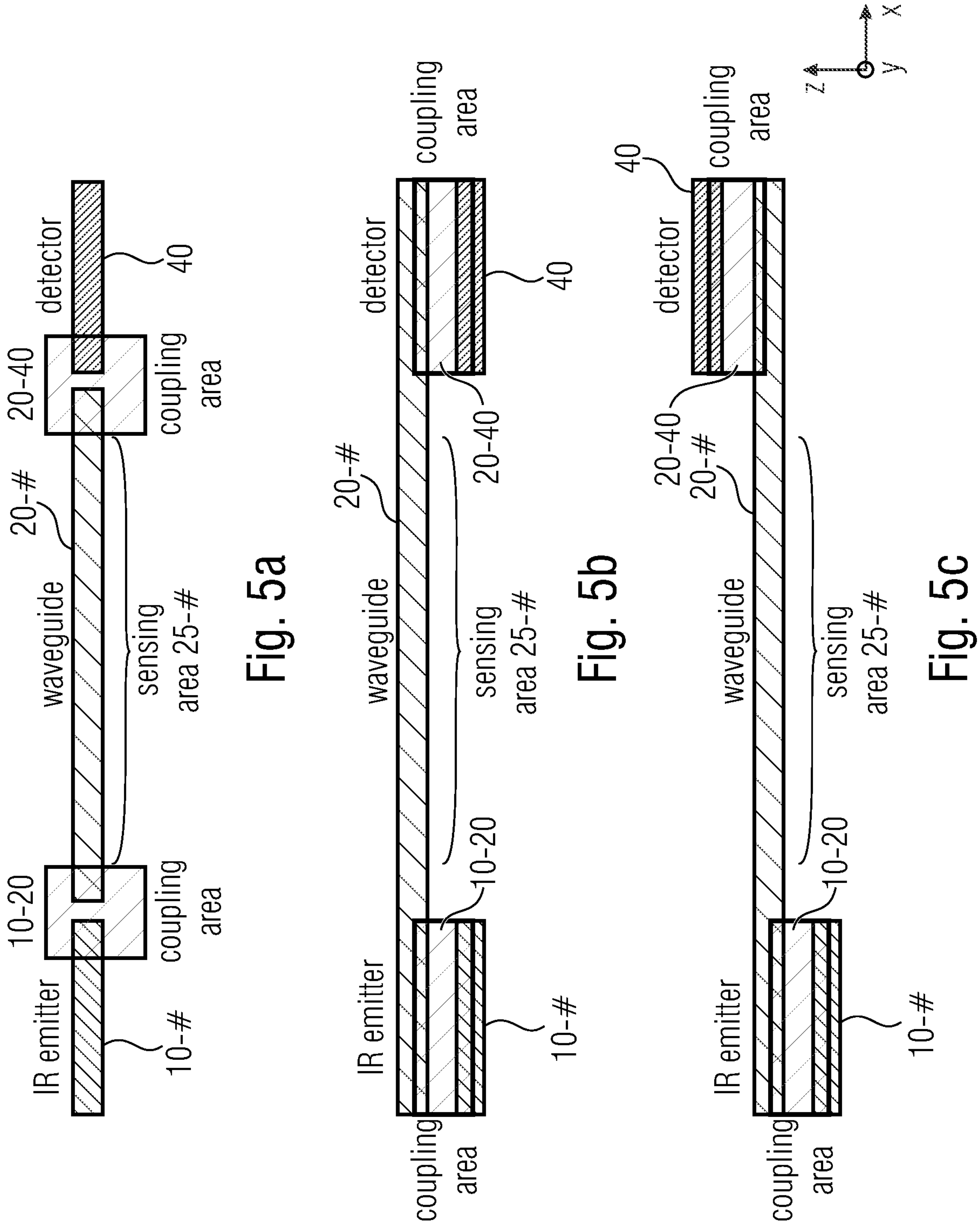
FIGS. 5*a*-5*c* show respective schematic cross-sectional views of different implementations of a fluid sensor according to different embodiments.

FIGS. 5a-5c show schematic cross-sectional views of different implementations of the arrangement of one of the plurality of "sections" of the fluid sensor 100 according to an embodiment.

According to a further embodiment, the thermal radiation emitters 10-1, . . . , 10-# may comprise a semiconductor strip (wire) having a main emission surface region emitting the broadband thermal radiation R in a main radiation emission direction and parallel or vertical to the waveguide structure. According to a further embodiment, the coupling direction between the waveguide structure 20 and the thermal detector 40 may be parallel (in-plane) or vertical to the propagation direction of to the waveguide structure. The coupling area 10-20 is respectively between the thermal emitter 10-# and the waveguide structure 20-#, and the coupling area 20-30 is respectively between the waveguide structure 20-# and the thermal detector 40.

As exemplarily shown in FIG. 5a, the coupling direction between the thermal emitter 10-# and the waveguide structure 20-# and the coupling direction between the waveguide structure 20-# and the thermal detector 40 may be parallel (in-plane) to the propagation direction of to the waveguide structure 20. Thus, the thermal emitter 10-#, the waveguide structure 20-# and the thermal detector 40 may be arranged in the same plane.

As exemplarily shown in FIGS. 5b-5c, the coupling direction between the thermal emitter 10-# and the waveguide structure 20-# and the coupling direction between the waveguide structure 20-# and the thermal detector 40 may be vertical (up and/or down) to the propagation direction of to the waveguide structure 20. As shown in FIG. 5b, the thermal emitter 10-# and the thermal detector 40 may be arranged in the same (first) plane, where the waveguide structure 20-# may be arranged in a further (second) plane. As shown in FIG. 5c, the thermal emitter 10-#, the waveguide structure 20-# and the thermal detector 40 may be arranged in the three different planes.

As already mentioned above, the fluid senor 100 may also be implemented as a multi-fluid sensor, if different filter elements (e.g. photonic crystal filters) 30-1, . . . , 30-# are used after the heaters 10-1, . . . , 10-#. Thus, multi gas measurements can be, for example, for measuring the ratio of carbon dioxide $CO_2$ and ozone $O_3$ as the different target gases (fluids) $F_T$ in the surrounding atmosphere.

Thus, the fluid sensor 100 as described with respect to FIGS. 1-5 may be implemented as a multi-fluid sensor. The above evaluations of FIGS. 1 to 5 of the elements of the fluid sensor device 100 and of the functionality thereof are applicable to the corresponding elements of the multi-fluid sensor 100.

Thus, a multi-fluid sensor can comprise the fluid sensor 100 as described above, where the waveguide structure 10 comprises a plurality of waveguides 20-1, . . . , 20-#, where a respective one of the plurality of thermal radiation emitters 10-1, . . . , 10-# is optically coupled to a respective one of the plurality of waveguides 20-1, . . . , 20-#, and where the optical filter structure 30 comprises a plurality of optical filter elements 30-1, . . . , 30-#.

A first group of the optical filter elements 30-1, . . . , 30-#, which is optically coupled to a first group of the plurality of waveguides 20-1, . . . , 20-#, is configured to filter the broadband thermal radiation R of the first group of thermal radiation emitters 10-1, . . . , 10-# to provide a filtered thermal radiation RE having a first center wavelength $\lambda_1$, and a second group of the optical filter elements 30-1, . . . , 30-#, which is optically coupled to a second group of the plurality of waveguides 20-1, . . . , 20-#, is configured to filter the broadband thermal radiation R of the second group of thermal radiation emitters 10-1, . . . , 10-# to provide a filtered thermal radiation $R_{F2}$ having a second center wavelength $\lambda_2$.

According to an embodiment, the first center wavelength $\lambda_1$ corresponds to an absorption band of a first target fluid $F_{T1}$, and where the second center wavelength $\lambda_2$ corresponds to an absorption band of a second target fluid $F_{T2}$. Although examples of the multi-fluid sensor are described with respect to two target gases, different numbers of target gases may be detected in various embodiments.

According to an embodiment, the operating temperature $T_1$ of the first group of the plurality of thermal radiation emitters 10-1, . . . , 10-#, which is optically coupled to the first group of the plurality of waveguides 20-1, . . . , 20-#, is adjusted so that an absorption band or spectral line of a first target fluid $F_{T1}$ is within a (tolerance) range of ±10% or ±2% at a peak intensity value of the IR emission spectrum of the first group of the plurality of thermal radiation emitters 10-1, . . . , 10-#.

The operating temperature $T_2$ of a second group of the plurality of thermal radiation emitters 10-1, . . . , 10-#, which is optically coupled to the second group of the plurality of waveguides 20-1, . . . , 20-#, is adjusted so that an absorption band or spectral line of a second target fluid $T_{F2}$ is within a (tolerance) range of ±10% or ±2% at a peak intensity value of the IR emission spectrum of the second group of the plurality of thermal radiation emitters 10-1, . . . , 10-#.

Additional embodiments and aspects are described which may be used alone or in combination with the features and functionalities described herein.

According to an embodiment, a fluid sensor for detecting a target fluid comprises a plurality of thermal radiation emitters for emitting a broadband thermal radiation, a waveguide structure configured to guide the emitted thermal radiation emitted from the plurality of thermal radiation emitters, where the guided thermal radiation comprises an evanescent field component for interacting with the surrounding atmosphere comprising the target fluid, an optical filter structure coupled to the waveguide structure, where the optical filter structure is configured to filter the broadband thermal radiation emitted by the thermal radiation emitter and to provide a filtered thermal radiation having a center wavelength ($\lambda_o$), a thermal radiation detector configured to provide a detector output signal based on a radiation strength of the filtered thermal radiation received from the waveguide structure, and an actuation device for connecting the plurality of thermal radiation emitters with a power source for providing the thermal radiation emitters in an actuated condition with electric energy so that the plurality of thermal radiation emitters has an operating temperature between 400 to 1300 K.

According to an embodiment, the operating temperature of the plurality of thermal radiation emitters is adjusted so that an absorption band or spectral line of the target fluid is within a range of ±10% at a peak intensity value of the IR emission spectrum of the plurality of thermal radiation emitters.

According to an embodiment, the operating temperature of the plurality of thermal radiation emitters is adjusted to be between 550 K and 800 K or between 620 K and 720 K so that an absorption band or spectral line of carbon dioxide ($CO_2$) as the target fluid or of ozone ($O_3$) as the target fluid is within a tolerance range of +10% at a peak intensity value of the IR emission spectrum of the plurality of thermal radiation emitters.

According to an embodiment, the waveguide structure comprises a plurality of waveguides, where a respective one of the plurality of thermal radiation emitters is optically coupled to one of the plurality of waveguides, and where the outputs of the plurality of waveguides are coupled to the thermal radiation detector.

According to an embodiment, the plurality of waveguides are arranged in a star-shaped, radial or radiant configuration, and where the outputs of the plurality of waveguide are directed to a center region of the fluid sensor.

According to an embodiment, the thermal radiation detector is arranged at a center region of the fluid sensor.

According to an embodiment, the thermal radiation detector is formed as a polygon, so that a respective one of the plurality of waveguides reaches one of the polygon edges of the detector in an orthogonal angle.

According to an embodiment, the waveguide structure comprises a joint waveguide, where the broadband thermal radiation of the plurality of thermal radiation emitters is coupled into the joint waveguide, and where the output of the joint waveguide is coupled to the thermal radiation detector.

According to an embodiment, the optical filter structure comprises a plurality of optical filter elements, where each of the plurality of waveguides comprises at least one of the optical filter elements to filter the broadband thermal radiation and to provide the filtered thermal radiation having the center wavelength ($\lambda_o$).

According to an embodiment, the optical filter structure is formed as an optical resonator structure having a narrow transmission band with a center wavelength $\lambda_o$, and where the optical filter structure comprises a photonic crystal structure or a Bragg filter structure as wavelength selective optical elements for providing the filtered thermal radiation having the center wavelength.

According to an embodiment, the thermal radiation emitters comprise a semiconductor strip having a main emission surface region emitting a broadband thermal radiation in a main radiation emission direction and parallel to the waveguide structure.

According to an embodiment, the waveguide structure comprises a strip waveguide, a slap waveguide, a slot waveguide or a rip waveguide.

According to an embodiment, the thermal radiation detector comprises a pyroelectric temperature sensor, a piezoelectric temperature sensor, a pn-junction temperature sensor or a resistive temperature sensor.

According to an embodiment, a multi-fluid sensor comprises the above fluid sensor, where the waveguide structure comprises a plurality of waveguides, where a respective one of the plurality of thermal radiation emitters is optically coupled to a respective one of the plurality of waveguides, and where the optical filter structure comprises a plurality of optical filter elements, where a first group of the optical filter elements, which is optically coupled to a first group of the plurality of waveguides, is configured to filter the broadband thermal radiation of the first group of thermal radiation emitters to provide a filtered thermal radiation having a first center wavelength ($\lambda_1$), and where a second group of the optical filter elements, which is optically coupled to a second group of the plurality of waveguides, is configured to filter the broadband thermal radiation of the second group of thermal radiation emitters to provide a filtered thermal radiation having a second center wavelength ($\lambda_2$).

According to an embodiment, the first center wavelength ($\lambda_1$) corresponds to an absorption band of a first target fluid, and where the second center wavelength ($\lambda_2$) corresponds to an absorption band of a second target fluid.

According to an embodiment, the operating temperature of the first group of the plurality of thermal radiation emitters, which is optically coupled to the first group of the plurality of waveguides, is adjusted so that an absorption band or spectral line of a first target fluid is within a range of ±10% at a peak intensity value of the IR emission spectrum of the first group of the plurality of thermal radiation emitters, and where the operating temperature of a second group of the plurality of thermal radiation emitters, which is optically coupled to the second group of the plurality of waveguides, is adjusted so that an absorption band or spectral line of a second target fluid is within a range of ±10% at a peak intensity value of the IR emission spectrum of the second group of the plurality of thermal radiation emitters.

Although some aspects have been described as features in the context of an apparatus it is clear that such a description may also be regarded as a description of corresponding features of a method. Although some aspects have been described as features in the context of a method, it is clear that such a description may also be regarded as a description of corresponding features concerning the functionality of an apparatus.

As disclosed herein, a fluid sensor detects a target fluid and comprises thermal radiation emitters emitting a broadband thermal radiation, a waveguide structure guiding the thermal radiation comprising an evanescent field component, an optical filter structure coupled to the waveguide structure to provide a filtered thermal radiation having a center wavelength, a thermal radiation detector configured to provide a detector output signal based on a radiation strength of the filtered thermal radiation, and an actuation device for connecting the plurality of thermal radiation emitters with a power source such that the plurality of thermal radiation emitters has an operating temperature between 400 to 1300 K.

In the foregoing Detailed Description, it can be seen that various features are grouped together in exemplary embodiments. It is noted that subject matter of disclosure may be present in less than all features of a single disclosed embodiment. It is also noted that the disclosure may also include a combination of a dependent claim with the subject matter of other dependent claims, or a combination of features with other dependent or independent claims. Furthermore, the disclosure may include features of a claim combined with any other independent claim.

The above described embodiments are merely illustrative for the principles of the present disclosure. It is noted that modifications and variations of the arrangements and the details described herein are contemplated as being a part of the disclosure.

What is claimed:

1. A fluid sensor comprising:

a plurality of thermal radiation emitters configured to emit a broadband thermal radiation;

a waveguide structure configured to guide the broadband thermal radiation, wherein the broadband thermal radiation comprises an evanescent field component for interacting with a surrounding atmosphere comprising a target fluid;

an optical filter structure coupled to the waveguide structure, wherein the optical filter structure is configured to filter the broadband thermal radiation and to provide a filtered thermal radiation having a center wavelength;

a thermal radiation detector configured to provide a detector output signal based on a radiation strength of the filtered thermal radiation; and an actuation device connecting the plurality of thermal radiation emitters to a power source configured to provide electrical energy to the thermal radiation emitters such that the plurality of thermal radiation emitters has an operating temperature between 400 K to 1300 K, wherein the operating temperature is adjustable for different ones of the plurality of thermal radiation emitters such that an absorption band or a spectral line of the target fluid is within a wavelength range of ±10% of an emission wavelength at a peak intensity value of an IR emission spectrum.

2. The fluid sensor of claim 1, wherein the operating temperature is adjustable between 550K and 800K such that the absorption band or the spectral line of the target fluid is within the wavelength range of ±10% of the emission wavelength at the peak intensity value of the IR emission spectrum of the plurality of thermal radiation emitters, and wherein the target fluid is carbon dioxide ($CO_2$) or ozone ($O_3$).

3. The fluid sensor of claim 1, wherein the waveguide structure comprises a plurality of waveguides, wherein each of the plurality of thermal radiation emitters is respectively optically coupled to each of the plurality of waveguides, and wherein outputs of the plurality of waveguides are respectively coupled to the thermal radiation detector.

4. The fluid sensor of claim 3, wherein the plurality of waveguides are arranged in a star-shaped, radial or radiant configuration, and wherein the outputs of the plurality of waveguides are directed to a center region of the fluid sensor.

5. The fluid sensor of claim 3, wherein the thermal radiation detector is arranged at a center region of the fluid sensor.

6. The fluid sensor of claim 5, wherein the thermal radiation detector is formed as a polygon, such that a respective one of the plurality of waveguides reaches a polygon edge of the thermal radiation detector at an orthogonal angle.

7. The fluid sensor of claim 1, wherein the waveguide structure comprises a joint waveguide, wherein the broadband thermal radiation is coupled into the joint waveguide, and wherein an output of the joint waveguide is coupled to the thermal radiation detector.

8. The fluid sensor of claim 3, wherein the optical filter structure comprises a plurality of optical filter elements, wherein each of the plurality of waveguides comprises at least one of the optical filter elements.

9. The fluid sensor of claim 1, wherein the optical filter structure is formed as an optical resonator structure having a narrow transmission band with the center wavelength, and wherein the optical filter structure comprises a photonic crystal structure or a Bragg filter structure as wavelength selective optical elements for providing the filtered thermal radiation having the center wavelength.

10. The fluid sensor of claim 1, wherein the thermal radiation emitters comprise a semiconductor strip having a main emission surface region emitting the broadband thermal radiation in a main radiation emission direction and parallel to the waveguide structure.

11. The fluid sensor of claim 1, wherein the waveguide structure comprises at least one of a strip waveguide, a slot waveguide, or a rip waveguide.

12. The fluid sensor of claim 1, wherein the thermal radiation detector comprises at least one of a pyroelectric temperature sensor, a piezoelectric temperature sensor, a pn junction temperature sensor, or a resistive temperature sensor.

13. A fluid sensor comprising:

a plurality of thermal radiation emitters configured to emit a broadband thermal radiation;

a waveguide structure configured to guide the broadband thermal radiation, wherein the broadband thermal radiation comprises an evanescent field component for interacting with a surrounding atmosphere comprising at least two target fluids, the waveguide structure comprising a plurality of waveguides, wherein each of the plurality of thermal radiation emitters is respectively optically coupled to each of the plurality of waveguides;

an optical filter structure coupled to the waveguide structure, wherein the optical filter structure is configured to filter the broadband thermal radiation and to provide a filtered thermal radiation, the optical filter structure comprising a plurality of optical filter elements;

a thermal radiation detector configured to provide a detector output signal based on a radiation strength of the filtered thermal radiation; and an actuation device connecting the plurality of thermal radiation emitters to a power source configured to provide electrical energy to the thermal radiation emitters, wherein a first group of the optical filter elements is optically coupled to a first group of the plurality of waveguides and is configured to provide the filtered thermal radiation having a first center wavelength, wherein a second group of the optical filter elements is optically coupled to a second group of the plurality of waveguides and is configured to provide the filtered thermal radiation having a second center wavelength different from the first center wavelength, wherein the first center wavelength corresponds to a first absorption band of a first target fluid and the second center wavelength corresponds to a second absorption band of a second target fluid, wherein a first group of the plurality of thermal radiation emitters is optically coupled to the first group of the plurality of waveguides, and a first operating temperature of the first group of the plurality of thermal radiation emitters is adjustable such that the first absorption band of the first target fluid is within a first wavelength range of ±10% of a first emission wavelength at a first peak intensity value of a first IR emission spectrum of the first group of the plurality of thermal radiation emitters, and wherein a second group of the plurality of thermal radiation emitters is optically coupled to the second group of the plurality of waveguides, and a second operating temperature of the second group of the plurality of thermal radiation emitters is adjustable independently from the first operating temperature such that the second absorption band of the second target fluid is within a second wavelength range of ±10% of a second emission wavelength at a second peak intensity value of a second IR emission spectrum of the second group of the plurality of thermal radiation emitters.

14. A method of operating a fluid sensor, the method comprising:

emitting a broadband thermal radiation using a plurality of thermal radiation emitters;

guiding the broadband thermal radiation using a waveguide structure, wherein the broadband thermal radiation comprises an evanescent field component for interacting with a surrounding atmosphere comprising a target fluid;

filtering the broadband thermal radiation using an optical filter structure coupled to the waveguide structure, wherein the optical filter structure is configured to provide a filtered thermal radiation having a center wavelength;

providing a detector output signal based on a radiation strength of the filtered thermal radiation using a thermal radiation detector, wherein the plurality of thermal radiation emitters are connected to a power source via an actuation device, the power source providing electrical energy to the thermal radiation emitters such that the plurality of thermal radiation emitters has an operating temperature between 400 K to 1300 K; and adjusting the operating temperature for different ones of the plurality of thermal radiation emitters such that an absorption band or a spectral line of the target fluid is within a wavelength range of ±10% of an emission wavelength at a peak intensity value of an IR emission spectrum.

15. The method of claim 14, further comprising:

adjusting the operating temperature between 550K and 800K such that the absorption band or the spectral line of the target fluid is within the wavelength range of ±10% of the emission wavelength at the peak intensity value of the IR emission spectrum of the plurality of thermal radiation emitters, and wherein the target fluid is carbon dioxide ($CO_2$) or ozone ($O_3$).

16. The method of claim 14, wherein the waveguide structure comprises at least one of a strip waveguide, a slot waveguide, or a rip waveguide, and wherein the thermal radiation detector comprises at least one of a pyroelectric temperature sensor, a piezoelectric temperature sensor, a pn junction temperature sensor, or a resistive temperature sensor.

17. The fluid sensor of claim 1, wherein the operating temperature is adjustable between 620K and 720K such that the absorption band or the spectral line of the target fluid is within the wavelength range of ±10% of the emission wavelength at the peak intensity value of the IR emission spectrum of the plurality of thermal radiation emitters, and wherein the target fluid is carbon dioxide ($CO_2$).

18. The fluid sensor of claim 1, wherein the operating temperature is adjustable between 620K and 720K such that the absorption band or the spectral line of the target fluid is within the wavelength range of ±10% of the emission wavelength at the peak intensity value of the IR emission spectrum of the plurality of thermal radiation emitters, and wherein the target fluid is ozone ($O_3$).

19. The method of claim 14, further comprising:

adjusting the operating temperature between 620K and 720K such that the absorption band or the spectral line of the target fluid is within the wavelength range of ±10% of the emission wavelength at the peak intensity value of the IR emission spectrum of the plurality of thermal radiation emitters, and wherein the target fluid is carbon dioxide ($CO_2$).

20. The method of claim 14, further comprising:

adjusting the operating temperature between 620K and 720K such that the absorption band or the spectral line of the target fluid is within the wavelength range of ±10% of the emission wavelength at the peak intensity value of the IR emission spectrum of the plurality of thermal radiation emitters, and wherein the target fluid is ozone ($O_3$).

* * * * *